United States Patent [19]

Detaille

[11] 4,021,921
[45] May 10, 1977

[54] DEVICE FOR TREATING THE PULP-CANALS OF A TOOTH

[76] Inventor: Louis J. Detaille, Chaussee de Dinant, 119, B-5150 Wepion, Belgium

[22] Filed: Oct. 17, 1975

[21] Appl. No.: 623,219

[30] Foreign Application Priority Data

Oct. 18, 1974 Belgium .............................. 44786

[52] U.S. Cl. ............................................ 32/40 R
[51] Int. Cl.[2] ........................................ A61C 3/00
[58] Field of Search ........................... 32/57, 40 R

[56] References Cited

UNITED STATES PATENTS

| 860,555 | 7/1907 | Middaugh | 32/40 R |
| 3,919,775 | 11/1975 | Malmin | 32/57 |

*Primary Examiner*—Robert Peshock
*Attorney, Agent, or Firm*—Sughrue, Rothwell, Mion, Zinn & Macpeak

[57] ABSTRACT

The invention relates to a device for treating the pulp-canals and -chamber of a tooth, the crown of which presents a previously opened pulp-chamber in which said canals open, comprising an apparatus tightly adaptable to the crown of the tooth and providing in the pulp-chamber and the pulp-canals of said tooth for the circulation of a treating solution acting substantially upon the vasculo-nervous bundle or the necrotic magma of the tooth, the pressure of the treating solution being subjected within the pulp-chamber and the pulp-canals to periodical impulses combined to oscillations of substantially higher frequency.

23 Claims, 7 Drawing Figures

DEVICE FOR TREATING THE PULP-CANALS OF A TOOTH

FIELD OF THE INVENTION

The present invention relates to a device for treating the pulp-canals of a tooth, the crown of which comprises a previously opened pulp-chamber wherein said canals open.

PRIOR ART

The nearly daily treatment of the pulp-canals raises a problem to the specialists of the dental art.

The tooth to be treated is either living and its canal(s) contain a vasculo-nervous bundle, or is dead and its canal(s) then contain a necrotic magma. A tooth can be mono- or pluri-rooted. The treatment consists in removing the vasculo-nervous bundle or the necrotic magma from the pulp-canal(s) and the pulp-chamber.

The current technique for treating the pulp-canals, which are particularly fine and of intricated form, mainly with regard to the molars, consists in using more or less thick rods fitted with metal-bristles or in form of rasps or files of various gauges. Said technique comprises mechanically withdrawing the vasculo-nervous bundle or the necrotic magma from the pulp canals while boring their size and this with hand-instruments possibly mounted on a rotative implement.

The presently known technique has many drawbacks.

Because of the extreme fineness and the irregular form of the pulp-canals, it is very difficult to enter into all the pulp-canals and to remove therefrom the vasculo-nervous bundle or the necrotic magma.

In the case of pulp-canals which are difficult of access, the duration of the treatment is particularly long and may require many hours for one tooth only.

In the event of strongly bent pulp-canals, the used instrument may break therein and this may require pulling the tooth.

In the case of pulp-canals also strongly bent, the instrument which is used does not follow each time the curvature of the canal and may progress in straight line in the hard substance of the tooth, so as to develop an irreversible wrong canal.

When introducing an instrument having a gauge corresponding accurately to the size of the pulp-canal, it happens that the vasculo-nervous bundle or the necrotic magma is partially pressed back towards the apex of the root and even beyond said apex, i.e. into the bone of the periapical area.

Some pulp-canals are so fine that no instrument can treat them mechanically.

From the above-mentioned drawbacks, it is seen that it is extremely difficult to efficiently and rationally treat all the pulp-canals of a tooth.

DETAILED DESCRIPTION OF THE INVENTION

In accordance with this invention, it is proposed to substitute for the mechanical treatment of the pulp-canals, an automatic biochemical and physical treatment consisting substantially in causing a treatment solution which reacts with the vasculo-nervous bundle or with the necrotic magma, to enter into said pulp-canals and to flow in the pulp-chamber and -canals. In view of the chemical action of the used treatment solution, the vasculo-nervous bundle or the necrotic magma is decomposed and gradually dissolved. Furthermore, owing to the hydraulic action of said solution maintained in forced circulation, this charged solution is efficiently expelled from the pulp-canals and -chamber. The treatment device according to the invention has also the great advantage of avoiding the use of any mechanical intracanalar implement having the above-named drawbacks.

The pulp-canal treating device according to the invention in fact comprises an apparatus tightly adaptable to the crown of the tooth and providing in the pulp-chamber and in the canal(s) for the circulation of a treating solution acting namely upon the vasculo-nervous bundle or the necrotic magma. In order to have this apparatus working particularly efficiently, it is of advantage that the treating solution pressure is subjected to periodical impulses combined with oscillations of substantially higher frequency in the pulp-chamber and -canal(s).

The terms "periodical impulses" relate to pressure changes of elevated amplitude and of small frequency, whereas the terms "frequency oscillations" relate to frequency variations of small amplitude and of high frequency, both pressure modifications being combined in such a manner that the frequency oscillations are carried by the periodical pressure impulses.

Tests have shown that, when the treating or treatment solution is only subjected to periodical pressure impulses, said solution does not reach the end (apex) of the pulp-canals. In the bottom of said canals remains accordingly a necrotized vasculo-nervous bundle, which is dangerous for the apex or the splices of the pulp-canal(s) which may then undergo local infections.

Tests have also been made by subjecting the treating solution only to pressure oscillations of higher frequency. In this event also, said solution does not reach the extremity of the pulp-canals.

On the other hand, trials effected with a treatment solution the pressure of which was subjected to periodical impulses combined to substantially higher frequency oscillations, have demonstrated that said solution effectively reaches the apex or apices or the pulp-canal(s).

In order to further increase the efficiency of the new treating device, said apparatus may comprise means for admitting a gas, particularly air, oxygen or ozone, in the treating solution, before the introduction of said solution in the pulp-chamber.

Indeed, trials effected with a treatment solution into which air-, oxygen- or ozone-bubbles are admitted and the pressure whereof is subjected to the above-mentioned combination of impulses and oscillations have shown that the introduction of bubbles promotes and accelerates the complete expulsion of the content of the pulp-canal(s) and pulp-chamber.

It has been surprisingly found that the introduction of air in the solution has a synergistic effect on the treatment by causing a fast expulsion of the tooth contents. Normally, one should, on the contrary, expect that the introduction of a complementary amount of air in the system, would hinder or delay the removal of the vasculo-nervous bundle of the tooth, because of the presence of an increased amount of air in the system.

On the other hand, tests have also shown that the use of the apparatus according to the invention is perfectly painless. Furthermore, the patient feels no shocks, nor any discomfort when he undergoes the treatment. Said tests have also demonstrated that the pulp-canals and specially their apices, are in no way injured by said treatment. Although some people consider that the apex of a tooth is open, the tests have shown that there is practically no leak of liquid through the apex.

With regard to the duration of the treatment effected by means of the device according to the invention, some varies from about 1 to 6 minutes. At the end of the treatment, the vasculo-nervous bundle or the necrotic magma is totally removed from the pulp-chamber and the pulp-canals of the treated tooth.

Examination of the used treating solution has not shown the presence of fragments of the vasculo-nervous bundle or of the necrotic magma, suspended in said liquid. It seems that, under the effect of the physical and biochemical treatment of the solution, the material contained in the tooth is dissolved in said liquid.

In order to proceed with the treatment of the pulp-canals after the scouring by the treating solution, the new device provides furthermore for the circulation of a rinsing liquid in the pulp-canal(s) and -chamber, after the circulation of said treating solution. In the same field, after rinsing of the pulp-canals and -chamber, the apparatus provides also, in said pulp-canals and -chamber, for the circulation of a drying fluid, after the circulation of the rinsing liquid.

In practical use, the apparatus of the new treatment device substantially comprises a mouthpiece having a tapered part tightly engaged in the also tapered boring of a ring which can be fitted on the dental crown. The mouthpiece has an inlet for admitting the treatment solution towards the pulp-chamber and -canals and an outlet for the escape of said solution out of the tooth. In order to be able to distribute the treating solution in the pulp-chamber with the apparatus of the new device, the inlet of said solution in the mouthpiece comprises an inner chamber connected to the treating solution feeding pipe and communicating with the pulp-chamber and -canals through at least one distributing or dividing-aperture, whereas for enabling the escape of the treating solution from the pulp-chamber with said apparatus, the outlet of said solution in said mouthpiece merely comprises an exhaust-pipe connected to the return of said treating solution.

According to a preferred embodiment of the apparatus of the new device, the mouthpiece is tightly closed by a separate head. The mouthpiece and the head define the inner chamber. The side-wall of the mouthpiece comprises a treating solution inlet in the inner chamber and is machine-tapered on the part of its external face which is opposite to the head, whereas the bottom of the mouthpiece comprises the distributing- or dividing-aperture(s) of the treating solution, and an aperture for the exhaust-pipe as well. On the other hand, the exhaust-pipe extends through the inner chamber and is fixed to the head, at right angles with a treating solution outlet which is provided in said head.

In the new treatment device, the apparatus can be supplied with treating solution in various manners.

According to a first embodiment, the apparatus is supplied with treating solution from a feeding tank on the one hand, by the action of a driving pump which is subjected to periodical stoppings or slackenings in order to generate the pressure impulses of the treating solution and, on the other hand, under the control of a valve subjected to rapid variations of its passageway cross-section, so as to develop the pressure oscillations of the treatment solution.

If a gas, particularly air, oxygen or ozone, is to be included in the treating solution, or if a rinsing liquid or a drying fluid is to be substituted for the treatment solution, said gas, said liquid or said fluid is admitted through a feeding-pipe plugged in the feeding pipe of the treating solution, up-stream of the driving pump.

According to a second embodiment, the apparatus is supplied with treating solution from a feeding tank pressurized, on the one hand, by means of a gas, particularly air, oxygen or ozone, contained in said tank and admitted therein through a valve subjected to periodical variations of its passageway cross-section in order to generate the pressure impulses of the treatment solution and, on the other hand, under the control of another valve subjected to fast variations of its passageway cross-section, so as to develop the solution pressure oscillations.

If a gas, particularly air, oxygen or ozone, is to be included in the treatment solution in the new device, a part of said gas-stream, normally destined to the control tank, may be used therefor. Accordingly, a part of the fluid which has streamed through the control valve generating said pressure impulses of the treating solution, is withdrawn from the tank feeding-pipe, through a by-pass pipe plugged in the feeding-pipe of said solution downstream said control valve, so as to be included thereafter in said solution. If a rinsing liquid or a drying fluid is to be substituted for the treating solution in the new device, said liquid or said fluid is conveyed through a feeding pipe plugged in the feeding pipe of said solution, down-stream the tank.

Generally, in the new treatment device, it is preferred to operate with an output of the treating solution admitted into the pulp-chamber through the apparatus from about 50 to 200 cc/min., preferably from 50 to 100 cc/min. Furthermore, it is also advisable to use, for controlling the means for generating pressure impulses of the treating solution, i.e. the pump or the control valve, a pressure-regulator such as a pressostat acting alternatively thereupon, on the one hand, when said pressure reaches an upper value from 1 to 3 kg/cm$^2$, preferably 2 kg/cm$^2$, and, on the other hand, when said pressure reaches a lower value from 0 to 1 kg/cm$^2$, preferably 0.5 kg/cm$^2$. Furthermore, said pressostat is able to produce pressure impulses having a period comprised between 6 to 20 sec. On the other hand, it is also suitable to use for controlling the valve generating the pressure oscillations of the treatment solution, an electronic device known per se, such as an astable multivibrator with a monojunction transistor (Emploi rationnel des transistors, J.P. Oekmichen, Editions Radio, Paris), so to obtain oscillation frequencies from 0.6 to 2.5 Herz, preferably 1.33 Hertz, corresponding to 40 to 160 oscillations/minute, preferably 80 oscillations/minute.

According to the invention, the new treatment device and especially the corresponding apparatus, can also be used for injecting a curable past or fluid in the pulp-canals and -chamber, after the complete cleaning of same, so as to fill up said canals and chamber. In this case, the filling up paste or fluid flows through the feeding pipe provided for the treating solution, from a feeding tank subjected to the action of a pressurized gas, particularly air. In order to avoid the inclusion of gas-bubbles in said fluid or paste at the end of the filling up of the pulp-canals and -chamber, the pressurized gas-circuit, particularly the air-circuit, which feeds the fluid or paste tank, comprises also vent means actuated at the end of said filling up.

Other details and features of the invention will clearly appear from the following disclosure and the attached drawings which represent diagrammatically and by way of example only, two embodiments of the invention and wherein.

Figure 1:
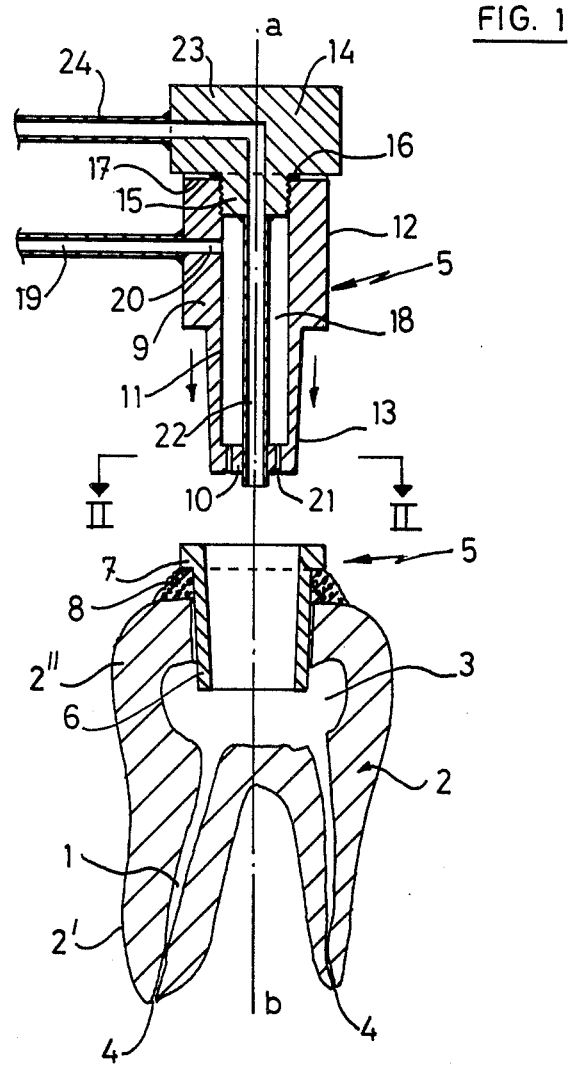
FIG. 1 is a vertical section view of the apparatus which is connected to the treatment device according to the invention, the lower part of said apparatus being set on a tooth to be treated, both lower and upper parts of said apparatus being mutually brought into line through the vertical axis ab.
Figure 2:
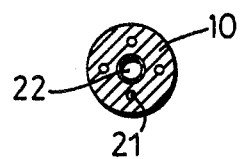
FIG. 2 is a horizontal section of the upper part of the apparatus, along the line II—II of FIG. 1.

Each shown device can be used for treating the pulp-canals 1 of a tooth 2 which comprises roots 2' and a crown 2" having a pulp-chamber 3 which is open at the level of the crown 2". The extremity or apex of the roots is indicated by reference numeral 4. The treatment of the pulp-canals 1 substantially consists in cleaning or scouring same with an appropriate solution, e.g. an aqueous solution containing 1.5 to 3.75 ‰, preferably 2 to 2.5 ‰, by weight, of chloramine. For this purpose, the treating solution is contacted with the content of pulp-chamber 3 and of the pulp-canals 1, consisting of a vasculo-nervous bundle or of a necrotic magma. The action of the treatment solution is both chemical (decomposition of the vasculo-nervous bundle or the necrotic magma of the pulp-canals 1 and -chamber 3) and hydraulic (removal the dissolved residues of said bundle or magma). If required, the treatment device can be adapted and completed for providing successively the rinsing of the pulp-canals 1 and of the pulp-chamber 3, with a rinsing liquid, after said cleaning, the drying of said canals 1 and said chamber 3 by means of a drying fluid, after said rinsing, and the filling up of said chamber 3 and of said canals 1 with a filling fluid or paste, after said drying.

The treatment device substantially comprises a treating apparatus 5 shown partly above the tooth 2 in FIG. 1. Said apparatus 5 is intended to be tightly mounted on the dental crown 2". The apparatus 5 is adapted to admit in the pulp-chamber 3 and from said chamber in the pulp-canals 1, mainly the treating solution and secondarily the rinsing liquid, the drying fluid and even the filling up paste or fluid.

The apparatus 5 comprises substantially two mutually tapering nestable parts.

The first part of the apparatus 5 consists of a ring 6 the inner faces of which are tapered. The ring 6 is advantageously provided with an upper flange 7. As shown in FIG. 1, said ring 6 mounted on the dental crown 2" is engaged in the inlet of the pulp-chamber 3.

The ring 6 is tightly and hermetically fitted to the crown 2" by means of a joint 8 made of an appropriate cement.

The second part of the apparatus 5 comprises a vertically elongated mouthpiece 9 having its bottom 10 towards the tooth. The inner face 11 of the mouthpiece 9 is cylindrical and upwardly tapped, while the upper part 12 of the outer face of said mouthpiece 9 is also cylindrical and the remaining lower part 13 of said mouthpiece 9 is tapered according to a taper angle corresponding to the taper angle of the ring 6.

The mouthpiece 9 is tightly closed by means of a head 14 having a lower threaded protrusion 15 threaded in the tapped part of said mouthpiece 9. A sealing joint 16 is provided between the head 14 and the upper face 17 of the mouthpiece 9.

After assembly, the mouthpiece 9 and the head 14 define an inner chamber 18 shown on FIG. 1. The inner chamber 18 communicates with a feeding pipe 19 through an inlet 20 provided in the side-wall of the mouthpiece 9. On the other hand, the inner chamber 18 presents at its lower part distributing or dividing apertures 21 extending through the bottom 10 of said mouthpiece 9. Apertures 21 consist in little holes regularly spaced about the vertical a–b axis of the apparatus 5, but said apertures may be constituted of a single annular aperture coaxial with said vertical axis a–b.

Through the inner chamber 18 extends coaxially an exhaust tube 22. The lower end of said tube 22 is fitted in a corresponding opening of the bottom 10 of the mouthpiece 9 and protrudes from said bottom 10. The upper end of the tube 22 is fixed to the head 14 coaxially with an outlet 23 which is bored in said head 14 and communicates with a return pipe 24.

Instead of two pieces, namely the mouthpiece 9 and the separate head 14, the apparatus 5 can be made as an integral part.

The upper part of the apparatus 5 is fitted in said ring 6 with the lower part of said mouthpiece 9 taperly and tightly nested in said ring 6. Accordingly, the upper part of the apparatus 5 when supplied with treating solution allows admittance of said solution in the pulp-chamber 3 and in the pulp-canals 1 and the escape of said solution from said pulp-canals 1 and said pulp-chamber 3. The treating solution supplied through the feeding pipe 19 flows through the apparatus 5 by means of an inlet passageway comprising the inlet 20, the inner chamber 18 and the distributing or dividing apertures 21. On the other hand, the treating solution flows out the canals 1 and the chamber 3 through an outlet passageway of the apparatus 5, comprising the tube 22 and the outlet 23, said solution being thereafter discharged through the return pipe 24.

Figure 3:
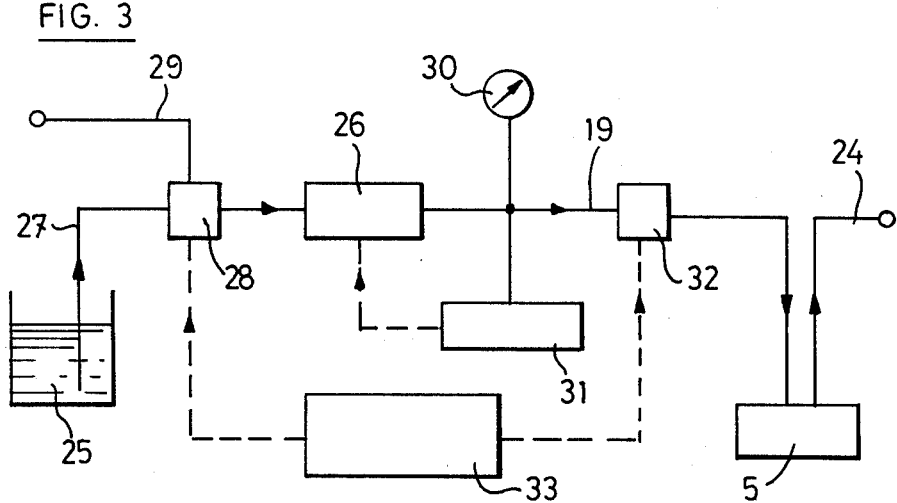
FIG. 3 is a diagrammatic view of a first embodiment of the new treatment device comprising the above-mentioned apparatus.

In the first embodiment illustrated in FIG. 3, the apparatus 5 is fed with treating solution from a feeding tank 25. The treatment solution is extracted from the tank 25 by a drive-pump 26, through a feeding pipe 27. The pump 26 comprises preferably, in a metal housing, a flexible hose allowing the passage of the treating solution and rotative rollers successively co-operating with said flexible hose, so as to temporarily reduce its section solely at the time of the advancing of said rollers against said hose thereby squeezing the hose against the housing and so carrying the treating solution therein.

In the embodiment shown in FIG. 3, the feeding pipe 27 is fitted with a three-way mixing valve 28 allowing the connection of a side pipe 29 which opens to the atmosphere. When rotating, the pump 26 sucks alternately treating solution and air and thereby carries a air-bubbles containing treating solution through the feeding pipe 19 connected to the apparatus 5. Down-stream the pump 26 is a pressure-gauge 30 which indicates the pressure of the treating solution, while a pressure regulator, such as a pressostat 31 controls, under the influence of said pressure, the working of the pump 26. In fact, said pressostat 31 acts upon the pump 26 between two limiting values of the pressure of the treating solution in said feeding pipe 19. When said pressure reaches an upper limit of about 1 to 3 $kg/cm^2$, preferably 2 $kg/cm^2$, the pressostat 31 causes the disengaging of the driving part of the pump 26 and thereby stops said pump. A pressure drop of the treating solution is thus caused in the feeding pipe 19. When the pressure reaches then a lower limit of about 0 to 1 $kg/cm^2$, preferably 0.5 $kg/cm^2$, the pressostat starts the driving part of the pump 26 which then works again. Thereby the pressure of the treating solution increases in the feeding pipe 19. Thereafter said process is alternately repeated, so that said pressostat combined to the pump 26 creates regular periodical impulses in the pressure of the treating solution flowing through the feeding pipe 19 and feeding the apparatus 5, said impulses having a low frequency and a long period of about 6 to 20 sec.

Down-stream the connections of the pressure-gauge 30 and of the pressostat 31, the feeding pipe 19 is provided with a two-way control valve 32. The cross-section of the passage of the control valve 32 varies swiftly between two limiting values, since the shutter of said valve 32 is controlled by an electronic vibratory system 33 known per se. Thereby, the control valve 32 generates in the circuit of the treating solution down-stream the pump 26, alternate narrowings and widenings having frequencies which are substantially greater than the frequencies of the impulses due to the movement of the pump 26, said higher frequencies being from 0.6 to 2.5 Herz, preferably 1.33 Herz, corresponding to 40 to 160 oscillations/minute, preferably 80 oscillations/minute. Thereby the stream of the treating solution which flows through the feeding pipe 19 beyond the control valve 32 and enters in the apparatus 5 is subjected, on the one hand, to periodical pressure impulses which have a low frequency and a long period and, on the other hand, to pressure oscillations which have a high frequency and a short period, due to the control valve 32. It is pointed out that the above-named mixing valve 28 may also be controlled by means of the electronic system 33 so as to include air-bubbles in said solution. In this case, the valve 32 can be omitted, since the inclusion of air-bubbles in the solution results in generating per se, the pressure oscillations, having a high frequency and a short period, in the solution within the tooth.

The treating solution the pressure of which is thereby doubly urged, is injected into the pulp-chamber 3 and the pulp-canals 1 by means of the apparatus 5, in an amount of 50 to 200 cc/min., preferably 50 to 100 cc/min. and circulates vigorously and efficiently in said chamber 3 so as to enter in said pulp-canals 1 and thereby act therein chemically and hydraulically before escaping therefrom while removing the dissolved residues through the same apparatus.

In the case where a rinsing liquid or a drying fluid is used after the cleaning of the pulp-chamber 3 and of the pulp-canals 1, the treatment device comprises a feeding tank for said liquid or fluid, similar to the above-mentioned tank 25. The pump then normally causes the flow of the rinsing liquid or the drying fluid through the feeding pipes 27 and 29 and the apparatus 5, in the pulp-chamber 3 and the pulp-canals 1 wherein said liquid can be distributed and moved in the same way as the treatment solution.

Figure 4:
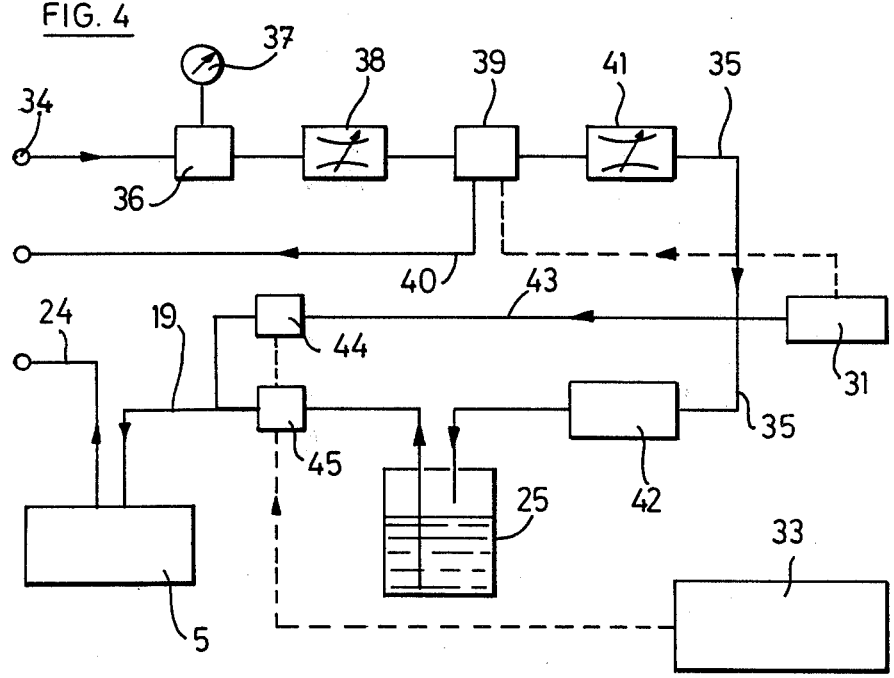
FIG. 4 is also a diagrammatic view of a second embodiment of the new treatment device with the above-named apparatus.

In the second embodiment shown in FIG. 4, the apparatus is supplied with treating solution from said feeding tank 25 which is subjected to a definite gaseous pressure instead of being subjected to the atmospheric pressure as was the case in the first embodiment. The gas pressure in said tank 25 generates the power needed for driving said treatment solution beyond the apparatus 5.

The active gas pressure in the feeding tank 25 is developed by a compressed gas, e.g. compressed air, from a feeding source 34, through a feeding pipe 35. The compressed and filtered air coming from the source 34 is first expanded in a pressure-reducer 36, fitted with a pressure-gauge 37 to a pressure of about 5 $kg/cm^2$. The speed of the air-flow is thereafter regulated by flowing through an adjustable speed regulator 38 which comprises substantially a variable neck in its passage-section, which adequately restrains the flow. After issuing from the regulator 38, the air-stream flows through a three-way control valve 39, the third way of which is vented to the atmosphere through an independent pipe 40. After passing through the control valve 39, the air-stream passes freely through a second speed regulator 41, similar to the preceding one, the function of which will be described herein after. The air-stream is introduced in a closed chamber 42. Between the second speed-regulator 41 and the chamber 42, a pressure regulator, such as a pressostat 31, is plugged in the feeding-pipe 35 of the compressed air.

In a first step, the control valve 39 is open, so that the compressed air issuing from the speed regulator 38 may flow freely through the speed regulator 41, thereby increasing the pressure in the chamber 42. The pressure increasing time is adjusted by means of the speed regulator 38. The pressostat 31 controls the shutter of the control valve 39, when the pressure reaches a maximum predetermined value in such a manner that the pipe 35 is vented to the atmosphere by means of the pipe 40. At this moment, the pressure decreases in the pipe 35 and the compressed air flows through the speed regulator 41 in a direction opposite to its moving direction during the pressure increasing period and so escapes through the pipe 40 in the atmosphere, thereby generating a pressure drop the duration of which is controlled by means of the speed regulator 41.

As in the first embodiment, the pressostat 31 reengages the shutter of the control valve 39, at the time where the pressure reaches a lower limit value in the feeding pipe 35. The chamber 42 contains thereby a volume of air which is always subjected to pressure changes of low frequency and of great period. Such pressure changes exist accordingly in the feeding tank 25.

The air stream of alternating variable pressure, forwarded in the feeding pipe 35, is divided in two portions. The first portion of the air stream is carried by a by-pass pipe 43 through a two-way control valve 44. On the other hand, the second portion of the air stream is sent to the closed chamber 42 and to the feeding tank 25. Said second portion of the air-stream allows the delivery of a treating solution stream through the feeding pipe 19 connecting said tank 25 to the apparatus 5, according to pressures varying in relation with the above-mentioned impulses. On the other hand, the by-pass pipe 43 opens in the feeding pipe 19 downstream a two-way control valve 45 fitted in said pipe 19. The control valves 44 and 45 are alternately controlled by the vibratory electronic system which is known per se, so as to be subjected to fast changes of their passage sections allowing the generation of pressure oscillations of high frequency and short period, in the treatment solution stream flowing through the feeding pipe 19. Before its admission in the apparatus 5, the compressed air admitted in the treating solution at the junction of pipes 43 and 19 forms a solution the pressure of which is subjected not only to periodical impulses of low frequency and long period, but also to oscillations having a high frequency and a short period. Once again, it is the combination of said pressure-impulses and pressure-oscillations that causes the treating solution introduced in the pulp-chamber 3 and -canals 1 through the apparatus 5 in an amount of 50 to 200 cc/minute, preferably 50 to 100 cc/minute, to act vigorously and efficiently until the end of the pulp-canals 1, in the same way as in the first embodiment.

Figure 5:
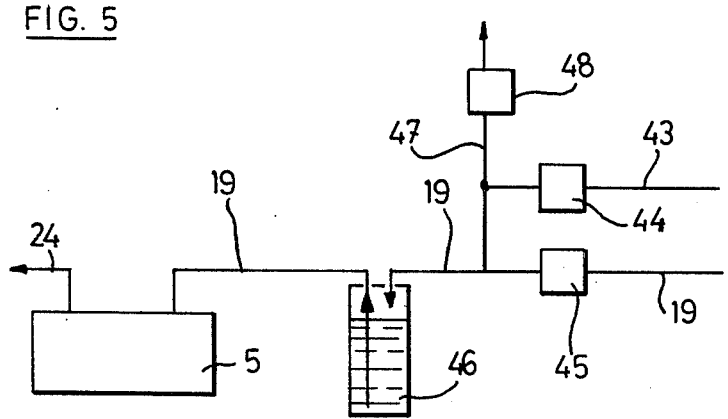
FIG. 5 is a diagrammatic view illustrating a complementary part of the device shown in FIG. 4, allowing the filling up of a tooth.

In the case where a rinsing liquid or a drying fluid is used after the cleaning or scouring, the treatment device comprises a feeding tank for said liquid or said fluid, that can be functionally substituted for the feeding tank 25. FIG. 5 shows a complementary part of the device shown in FIG. 4, allowing the filling up of the pulp-canals 1 and of the pulp-chamber 3 with a filling fluid or filling paste, after cleaning, rinsing and drying of said canals 1 and said chamber 3.

The treatment device comprises accordingly a feeding tank 46 containing a gradually curing or setting appropriate filling fluid or filling paste. An epoxy resin may, for example, be used as filling fluid.

The feeding tank 46 is plugged in the feeding pipe 19 which extends from the feeding tank 25 to the apparatus 5, the plugging being realized down-stream the junction of the treating solution- and compressed air-inlets.

The flow of the fluid or paste from the feeding tank 46 through the feeding pipe 19 and through the admission passage of the apparatus 5 is caused by the action of the pressurized air admitted in the upper part of said tank 46 above the filling paste or fluid. In the described example, the air generating the forwarding driving pressure of the filling fluid or paste is withdrawn from the above-named pipe 19, the control valve 45 being closed.

At the end of the filling of the pulp-chamber 3 and of the pulp-canals 1, the pressurized air-circuit is temporarily vented to the atmosphere in order to avoid the introduction of air in said apparatus 5 and the tooth 2, at the end of the process, when said tank 46 is nearly empty. For this purpose, there is provided a side pipe 47 plugged in the pipe 19 and opening to the atmosphere. The pipe 47 is provided with a two-way control valve 48 which is maintained closed during the major part of the filling process but opened at the end of said process.

Figure 7:
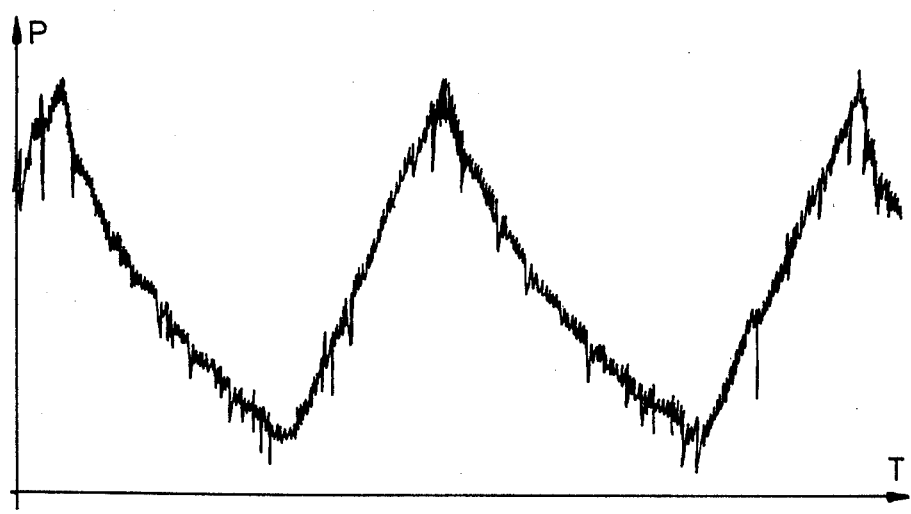
FIG. 7 is a diagram illustrating the evolution of the pressure (on the Y-axis) of the treating solution in relation with the time (on the X-axis), in a tooth, in the event where a gas is admitted in the treating solution.
Figure 6:
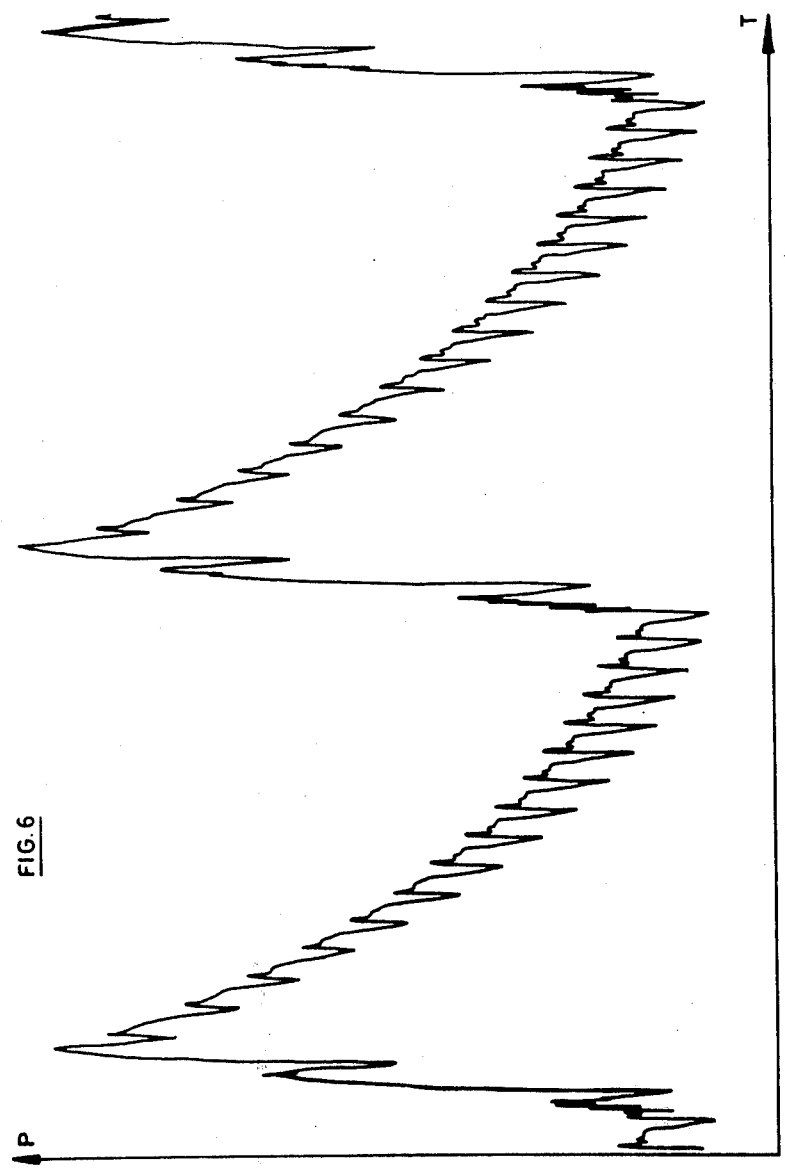
FIG. 6 is a diagram illustrating the evolution of the pressure (P on the Y-axis) of the treating solution in relation with the time (T on the X-axis), in a tooth, in the case where no gas is admitted in the treating solution.

A comparison of the pressure curves of FIGS. 6 and 7 shows the considerable effect of the inclusion of air-bubbles in the treating solution (FIG. 7) upon the high frequency- and short period-oscillations of the pressure of said solution.

I claim:

1. A device for treating the pulp-canals and -chamber of a tooth, the crown of which presents a previously opened pulp-chamber in which said canals open, said device comprising:
   an apparatus tightly adaptable to the crown of the tooth and closing the pulp-chamber,
   means for circulating a treating solution into the pulp-chamber and the pulp-canals, said treating solution acting substantially upon the vasculo-nervous bundle or the necrotic magma of the tooth,
   means for subjecting the pressure of the treating solution within the pulp-chamber and the pulp-canals to periodical impulses combined with oscillations of substantially higher frequency.

2. Device for treating the pulp-canals and -chamber of a tooth according to claim 1, comprising means for including a gas, particularly air, oxygen or ozone, in the treating solution before admitting said solution in the pulp-chamber and the pulp-canals.

3. Device for treating the pulp-canals and -chamber of a tooth according to claim 1, comprising means allowing the circulation of a rinsing liquid and/or of a drying fluid within said tooth.

4. Device for treating the pulp-canals and -chamber of a tooth according to claim 1, wherein said apparatus comprises substantially a mouthpiece comprising a tapered part tightly engaged in the also tapered boring of a ring which may be tightly fitted on the dental crown, said mouthpiece having an inlet passageway for admitting treating solution towards the pulp-chamber and the pulp-canals and an escape passageway for expelling said solution out of said pulp-chamber and said pulp-canals.

5. Device for treating the pulp-canals and -chamber of a tooth according to claim 4, wherein the inlet passageway of the treating solution in the mouthpiece comprises an inner chamber connected to a feeding pipe of said solution and communicating with the pulp-chamber and the pulp-canals through at least one aperture dividing or distributing said treating solution towards said chamber and said canals while the escape passageway of the treating solution in said mouthpiece comprises an exhaust pipe connected to the return pipe of said solution.

6. Device for treating the pulp-canals and -chamber of a tooth according to claim 5, wherein said mouthpiece is tightly closed by a head, said mouthpiece and said head defining the inner chamber and being machine-tapered about the part of its external face, which is opposite to the head, while the bottom of the mouthpiece comprises said treating solution dividing- or distributing-aperture, as well as an opening for the exhaust pipe which extends through the inner chamber and is fixed to the head, at right angles with a treating solution outlet which is provided in said head.

7. Device for treating the pulp-canals and -chamber of a tooth according to claim 1, wherein said apparatus is fed with treating solution from a feeding tank by the action of a driving pump which is subjected to periodical slackenings or stoppings thereby generating the treating solution pressure-impulses.

8. Device for treating the pulp-canals and -chamber of a tooth according to claim 7, comprising, in addition, at least one valve subjected to fast changes of its passage cross-section for developing said treating solution pressure-oscillations.

9. Device for treating the pulp-canals and -chamber of a tooth according to claim 8, wherein the driving pump comprises, within a housing, a flexible hose for the passage of the treating solution stream and rotative rollers successively cooperating with the flexible hose so as to temporarily reduce the section of same solely when said rollers are advancing against said hose, thereby squeezing said hose against the housing, the treating solution being so carried therein.

10. Device for treating the pulp-canals and -chamber of a tooth according to claim 2, wherein said gas, particularly air, oxygen or ozone, included in the treating solution, is admitted through an inlet pipe, plugged in the feeding pipe of the treating solution, upstream the driving pump.

11. Device for treating the pulp-canals and -chamber of a tooth according to claim 3, wherein the rinsing liquid and/or the drying fluid are substituted for the treating solution through an inlet pipe plugged in the feeding pipe of said solution, upstream the driving pump.

12. Device for treating the pulp-canals and -chamber of a tooth, according to claim 1 wherein said apparatus is fed with treating solution from a pressurized feeding tank, on the one hand, through the action of a gas, particularly air, contained in said tank and admitted therein through a control valve which is subjected to periodical variations of its passage cross-section thereby generating said treating solution pressure-impulses and, on the other hand, through the control of another control valve which is subjected to fast changes of its passage cross-section thereby generating the treating solution pressure-oscillations.

13. Device for treating the pulp-canals and -chamber of a tooth according to claim 12, wherein at the time of the pressure increase, the speed of the gas stream admitted in the feeding tank is regularized, for example through an adjustable speed regulator or neck, upstream the control valve.

14. Device for treating the pulp-canals and -chamber of a tooth according to claim 12, wherein the speed of the gas stream, at the time of the pressure decrease in the feeding tank, is regularized, for example through an adjustable speed regulator or neck positioned between the tank and the control valve.

15. Device for treating the pulp-canals and -chamber of a tooth according to claim 2, wherein a portion of the gas stream having flown through the control valve developing the treating solution pressure-impulses is withdrawn from the feeding pipe of the feeding tank through a by-pass pipe plugged in said feeding pipe downstream said control valve, so as to be included in said solution.

16. Device for treating the pulp-canals and -chamber of a tooth according to claim 3 comprising means for substituting a rinsing liquid and/or a drying fluid for said treating solution.

17. Device for treating the pulp-canals and -chamber of a tooth according to claim 1, wherein means for circulating a treating solution feeds the treating solution into pulp-chamber and pulp-canals, in an amount of 50 to 200 cc/minute, preferably 50 to 100 cc/minute.

18. Device for treating the pulp-canals and -chamber of a tooth according to claim 17, wherein the means generating the treating solution pressure-impulses, i.e. the pump or the control valve, are controlled by a pressure regulator acting, on the one hand, when said pressure reaches an upper value comprised between 1 and 3 $kg/cm^2$, preferably 2 $kg/cm^2$, and, on the other hand, when said pressure reaches a lower value comprised between 0 and 1 $kg/cm^2$, preferably 0.5 $kg/cm^2$.

19. Device for treating the pulp-canals and -chamber of a tooth according to claim 18, wherein the pressure regulator develops pressure impulses having a period comprised between 6 and 20 sec.

20. Device for treating the pulp-canals and -chamber of a tooth according to claim 19, wherein the control valve generating the treating solution pressure oscillations is controlled through an electronic device known per se and providing to said oscillations frequencies from 0.6 to 2.6 Herz, preferably 1.33 Herz, corresponding to 40 to 160 oscillations/minute, preferably 80 oscillations/minute.

21. Device for treating the pulp-canals and -chamber of a tooth according to claim 1 wherein said apparatus allows the introduction of a curing or setting filling-fluid or -paste into the pulp-chamber and -canals in order to fill up said pulp-chamber and -canals after the cleaning or scouring of same.

22. Device for treating the pulp-canals and -chamber of a tooth according to claim 21, wherein the filling-fluid or -paste flows through the treating solution feeding pipe, from a feeding tank which is subjected to a pressurized gas, particularly air.

23. Device for treating the pulp-canals and -chamber of a tooth according to claim 22, wherein the pressurized gas (particularly air)-circuit feeding said filling-fluid or -paste tank, comprises venting means opening in the atmosphere which are actuated at the end of the filling up of the pulp-chamber and -canals.

* * * * *